(12) United States Patent
Weitzner et al.

(10) Patent No.: US 10,695,536 B2
(45) Date of Patent: *Jun. 30, 2020

(54) CATHETER DRIVER SYSTEM

(71) Applicant: Auris Health, Inc., Redwood City, CA (US)

(72) Inventors: Barry Weitzner, Action, MA (US); Brian Murphy, Watertown, MA (US)

(73) Assignee: Auris Health, Inc., Redwood City, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 15/465,403

(22) Filed: Mar. 21, 2017

(65) Prior Publication Data

US 2017/0252540 A1    Sep. 7, 2017

Related U.S. Application Data

(63) Continuation of application No. 14/189,107, filed on Feb. 25, 2014, now abandoned, which is a
(Continued)

(51) Int. Cl.
*A61M 25/01*    (2006.01)
*A61B 18/14*    (2006.01)
(Continued)

(52) U.S. Cl.
CPC ......... *A61M 25/0133* (2013.01); *A61B 18/14* (2013.01); *A61B 18/1492* (2013.01);
(Continued)

(58) Field of Classification Search
None
See application file for complete search history.

(56) References Cited

U.S. PATENT DOCUMENTS 2,556,601 A    6/1951    Schofield
2,566,183 A    8/1951    Forss
(Continued)

FOREIGN PATENT DOCUMENTS

CN    101500470    8/2009
CN    102665590    9/2012
(Continued)

OTHER PUBLICATIONS

Ikuta, et al., "Shape Memory Alloy Servo Actuator System With Electric Resistance Feedback and Application for Active Endoscope", 1988 IEEE, CH2555-1/88/0000/0427-430.
(Continued)

*Primary Examiner* — Matthew Kremer
(74) *Attorney, Agent, or Firm* — Knobbe, Martens, Olson & Bear LLP (57) ABSTRACT

An apparatus for performing medical procedures on an anatomical body includes an extension with an element near its distal end to be extended into the body, and a driver that moves the extension axially into the body, and that causes flexure of the distal end of the extension. The movement and flexure of the extension is driven by the driver from the proximal end of the extension, and an electronic controller directs the operation of the driver.

18 Claims, 7 Drawing Sheets

Related U.S. Application Data continuation of application No. 12/111,119, filed on Apr. 28, 2008, now Pat. No. 8,684,952, which is a continuation of application No. 10/270,743, filed on Oct. 11, 2002, now Pat. No. 8,414,505, which is a continuation-in-part of application No. 10/216,067, filed on Aug. 8, 2002, now abandoned, and a continuation-in-part of application No. 10/023,024, filed on Nov. 16, 2001, now abandoned, and a continuation-in-part of application No. 10/011,371, filed on Nov. 16, 2001, now Pat. No. 7,090,683, and a continuation-in-part of application No. 10/011,449, filed on Nov. 16, 2001, now abandoned, and a continuation-in-part of application No. 10/010,150, filed on Nov. 16, 2001, now Pat. No. 7,214,230, and a continuation-in-part of application No. 10/022,038, filed on Nov. 16, 2001, now abandoned, and a continuation-in-part of application No. 10/012,586, filed on Nov. 16, 2001, now Pat. No. 7,371,210.

(60) Provisional application No. 60/332,287, filed on Nov. 21, 2001, provisional application No. 60/313,497, filed on Aug. 21, 2001, provisional application No. 60/293,346, filed on May 24, 2001, provisional application No. 60/276,152, filed on Mar. 15, 2001, provisional application No. 60/276,217, filed on Mar. 15, 2001, provisional application No. 60/276,086, filed on Mar. 15, 2001, provisional application No. 60/269,200, filed on Feb. 15, 2001.

(51) Int. Cl.
*A61B 34/30* (2016.01)
*A61B 17/00* (2006.01)
*A61B 34/00* (2016.01)

(52) U.S. Cl.
CPC ......... *A61B 34/30* (2016.02); *A61M 25/0113* (2013.01); *A61B 34/70* (2016.02); *A61B 2017/003* (2013.01); *A61B 2034/301* (2016.02); *A61B 2034/742* (2016.02); *A61M 25/0147* (2013.01)

(56) References Cited

U.S. PATENT DOCUMENTS

| | | |
|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,414,137 A | 12/1968 | Fortin |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,921,536 A | 11/1975 | Savage |
| 3,926,386 A | 12/1975 | Stahmann |
| 4,141,245 A | 2/1979 | Brandstetter |
| 4,241,884 A | 12/1980 | Lynch |
| 4,243,034 A | 1/1981 | Brandt |
| 4,294,254 A | 10/1981 | Chamness |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,604,016 A | 8/1986 | Joyce |
| 4,654,024 A | 3/1987 | Crittenden et al. |
| 4,688,555 A | 8/1987 | Wardle |
| 4,702,250 A | 10/1987 | Ovil et al. |
| 4,745,908 A | 5/1988 | Wardle |
| 4,750,475 A | 6/1988 | Yoshihashi |
| 4,784,150 A | 11/1988 | Voorhies et al. |
| 4,853,874 A | 8/1989 | Iwamoto et al. |
| 4,857,058 A | 8/1989 | Payton |
| 4,907,168 A | 3/1990 | Boggs |
| 4,941,454 A | 7/1990 | Wood et al. |
| 4,945,790 A | 8/1990 | Golden |
| 4,977,886 A | 12/1990 | Takehana et al. |
| 4,979,949 A | 12/1990 | Matsen, III et al. |
| 5,047,011 A | 9/1991 | Caron et al. |
| 5,052,402 A | 10/1991 | Bencini et al. |
| 5,072,361 A | 12/1991 | Davis et al. |
| 5,078,140 A | 1/1992 | Kwoh |
| 5,084,054 A | 1/1992 | Bencini et al. |
| 5,086,401 A | 2/1992 | Glassman et al. |
| 5,116,180 A | 5/1992 | Fung et al. |
| 5,154,717 A | 10/1992 | Matsen, III et al. |
| 5,172,700 A | 12/1992 | Bencini et al. |
| 5,174,276 A | 12/1992 | Crockard |
| 5,174,278 A | 12/1992 | Babkow |
| 5,184,601 A | 2/1993 | Putman |
| 5,207,128 A | 5/1993 | Albright |
| 5,217,003 A | 6/1993 | Wilk |
| 5,234,428 A | 8/1993 | Kaufman |
| 5,236,432 A | 8/1993 | Matsen, III et al. |
| 5,238,002 A | 8/1993 | Devlin et al. |
| 5,238,005 A | 8/1993 | Imran |
| 5,256,150 A | 10/1993 | Quiachon et al. |
| 5,271,381 A | 12/1993 | Ailenger et al. |
| 5,277,085 A | 1/1994 | Tanimura et al. |
| 5,287,861 A | 2/1994 | Wilk |
| 5,295,958 A | 3/1994 | Shturman |
| 5,299,288 A | 3/1994 | Glassman et al. |
| 5,339,799 A | 8/1994 | Kami et al. |
| 5,341,459 A | 8/1994 | Backes |
| 5,342,295 A | 8/1994 | Imran |
| 5,346,498 A | 9/1994 | Greelis et al. |
| 5,347,987 A | 9/1994 | Feldstein et al. |
| 5,350,101 A | 9/1994 | Godlewski |
| 5,350,355 A | 9/1994 | Sklar |
| 5,354,297 A | 10/1994 | Avitall |
| 5,368,015 A | 11/1994 | Wilk |
| 5,372,147 A | 12/1994 | Lathrop, Jr. et al. |
| 5,382,685 A | 1/1995 | Klein et al. |
| 5,382,885 A | 1/1995 | Salcudean et al. |
| 5,389,100 A | 2/1995 | Bacich et al. |
| 5,397,323 A | 3/1995 | Taylor et al. |
| 5,398,691 A | 3/1995 | Martin et al. |
| 5,402,801 A | 4/1995 | Taylor |
| 5,409,019 A | 4/1995 | Wilk |
| 5,410,638 A | 4/1995 | Colgate et al. |
| 5,417,210 A | 5/1995 | Funda et al. |
| 5,426,687 A | 6/1995 | Goodall et al. |
| 5,429,144 A | 7/1995 | Wilk |
| 5,447,149 A | 9/1995 | Kikawada et al. |
| 5,480,422 A | 1/1996 | Ben-Haim |
| 5,497,784 A | 3/1996 | Imran |
| 5,507,725 A | 4/1996 | Savage et al. |
| 5,515,478 A | 5/1996 | Wang |
| 5,520,644 A | 5/1996 | Imran |
| 5,524,180 A | 6/1996 | Wang et al. |
| 5,527,279 A | 6/1996 | Imran |
| 5,540,649 A | 7/1996 | Bonnell et al. |
| 5,553,198 A | 9/1996 | Wang et al. |
| 5,559,294 A | 9/1996 | Hoium et al. |
| 5,572,999 A | 11/1996 | Funda et al. |
| 5,606,979 A | 3/1997 | Hodgson |
| 5,618,294 A | 4/1997 | Aust et al. |
| 5,624,398 A | 4/1997 | Smith et al. |
| 5,626,553 A | 5/1997 | Frassica et al. |
| 5,626,595 A | 5/1997 | Sklar et al. |
| 5,631,973 A | 5/1997 | Green |
| 5,632,758 A | 5/1997 | Sklar |
| 5,634,897 A | 6/1997 | Dance et al. |
| 5,636,634 A | 6/1997 | Kordis et al. |
| 5,649,956 A | 7/1997 | Jensen et al. |

(56) References Cited

U.S. PATENT DOCUMENTS

| | | |
|---|---|---|
| 5,657,429 A | 8/1997 | Wang et al. |
| 5,667,476 A | 9/1997 | Frassica et al. |
| 5,674,279 A | 10/1997 | Wright et al. |
| 5,680,860 A | 10/1997 | Imran |
| 5,709,661 A | 1/1998 | Van Egmond |
| 5,749,362 A | 5/1998 | Funda et al. |
| 5,754,741 A | 5/1998 | Wang et al. |
| 5,759,153 A | 6/1998 | Webler et al. |
| 5,762,458 A | 6/1998 | Wang et al. |
| 5,767,840 A | 6/1998 | Selker |
| 5,779,623 A | 7/1998 | Bonnell |
| 5,784,542 A | 7/1998 | Ohm et al. |
| 5,792,135 A | 8/1998 | Madhani et al. |
| 5,800,333 A | 9/1998 | Liprie |
| 5,800,423 A | 9/1998 | Jensen |
| 5,807,377 A | 9/1998 | Madhani et al. |
| 5,808,665 A | 9/1998 | Green |
| 5,810,880 A | 9/1998 | Jensen et al. |
| 5,814,038 A | 9/1998 | Jensen et al. |
| 5,815,640 A | 9/1998 | Wang et al. |
| 5,821,920 A | 10/1998 | Rosenberg et al. |
| 5,823,993 A | 10/1998 | Lemelson |
| 5,825,982 A | 10/1998 | Wright et al. |
| 5,827,313 A | 10/1998 | Ream |
| 5,828,197 A | 10/1998 | Martin et al. |
| 5,833,656 A | 11/1998 | Smith et al. |
| 5,845,646 A | 12/1998 | Lemelson |
| 5,855,553 A | 1/1999 | Tajima et al. |
| 5,855,583 A | 1/1999 | Wang et al. |
| 5,860,992 A | 1/1999 | Daniel et al. |
| 5,861,024 A | 1/1999 | Rashidi |
| 5,868,755 A | 2/1999 | Kanner et al. |
| 5,876,325 A | 3/1999 | Mizuno et al. |
| 5,878,193 A | 3/1999 | Wang et al. |
| 5,904,667 A | 5/1999 | Falwell |
| 5,907,664 A | 5/1999 | Wang et al. |
| 5,921,968 A | 7/1999 | Lampropoulos et al. |
| 5,928,248 A | 7/1999 | Acker |
| 5,931,832 A | 8/1999 | Jensen |
| 5,950,629 A | 9/1999 | Taylor et al. |
| 5,954,692 A | 9/1999 | Smith et al. |
| 5,957,941 A | 9/1999 | Ream |
| 5,964,717 A | 10/1999 | Gottlieb et al. |
| 5,967,934 A | 10/1999 | Ishida et al. |
| 5,971,976 A | 10/1999 | Wang et al. |
| 5,976,122 A | 11/1999 | Madhani et al. |
| 6,001,108 A | 12/1999 | Wang et al. |
| 6,004,271 A | 12/1999 | Moore |
| 6,007,550 A | 12/1999 | Wang et al. |
| 6,007,560 A | 12/1999 | Gottlieb et al. |
| 6,024,695 A | 2/2000 | Taylor et al. |
| 6,033,378 A | 3/2000 | Lundquist et al. |
| 6,036,636 A | 3/2000 | Motoki et al. |
| 6,058,323 A | 5/2000 | Lemelson |
| 6,063,093 A | 5/2000 | Winston et al. |
| 6,063,095 A | 5/2000 | Wang et al. |
| 6,080,170 A | 6/2000 | Nash et al. |
| 6,080,181 A | 6/2000 | Jensen et al. |
| 6,083,170 A | 7/2000 | Ben-Haim |
| 6,084,371 A | 7/2000 | Kress et al. |
| 6,096,004 A | 8/2000 | Meglan et al. |
| 6,102,850 A | 8/2000 | Wang et al. |
| 6,102,920 A | 8/2000 | Sullivan et al. |
| 6,106,511 A | 8/2000 | Jensen |
| 6,120,433 A | 9/2000 | Mizuno et al. |
| 6,126,635 A | 10/2000 | Simpson et al. |
| 6,132,368 A | 10/2000 | Cooper |
| 6,132,441 A | 10/2000 | Grace |
| 6,146,355 A | 11/2000 | Biggs |
| 6,154,000 A | 11/2000 | Rastegar et al. |
| 6,156,005 A | 12/2000 | Theron |
| 6,171,234 B1 | 1/2001 | White et al. |
| 6,179,856 B1 | 1/2001 | Barbere |
| 6,185,478 B1 | 2/2001 | Koakutsu et al. |
| 6,197,017 B1 | 3/2001 | Brock et al. |
| 6,203,507 B1 | 3/2001 | Wadsworth et al. |
| 6,203,525 B1 | 3/2001 | Whayne et al. |
| 6,206,903 B1 | 3/2001 | Ramans |
| 6,221,070 B1 | 4/2001 | Tu et al. |
| 6,223,100 B1 | 4/2001 | Green |
| 6,231,518 B1 | 5/2001 | Grabek et al. |
| 6,231,565 B1 | 5/2001 | Tovey et al. |
| 6,233,504 B1 | 5/2001 | Das et al. |
| 6,236,432 B1 | 5/2001 | Lee |
| 6,245,020 B1 | 6/2001 | Moore et al. |
| 6,246,200 B1 | 6/2001 | Blumenkranz et al. |
| 6,267,781 B1 | 7/2001 | Tu |
| 6,269,819 B1 | 8/2001 | Oz et al. |
| 6,272,371 B1 | 8/2001 | Shlomo |
| 6,273,862 B1 | 8/2001 | Privitera et al. |
| 6,283,921 B1 | 9/2001 | Nix et al. |
| 6,287,297 B1 | 9/2001 | Woodruff et al. |
| 6,289,579 B1 | 9/2001 | Viza et al. |
| 6,290,675 B1 | 9/2001 | Vujanic et al. |
| 6,292,681 B1 | 9/2001 | Moore |
| 6,298,257 B1 | 10/2001 | Hall et al. |
| 6,309,397 B1 | 10/2001 | Julian et al. |
| 6,312,435 B1 | 11/2001 | Wallace et al. |
| 6,319,227 B1 | 11/2001 | Mansouri-Ruiz |
| 6,321,106 B1 | 11/2001 | Lemelson |
| 6,325,808 B1 | 12/2001 | Bernard et al. |
| 6,331,166 B1 | 12/2001 | Burbank et al. |
| 6,331,181 B1 | 12/2001 | Tierney et al. |
| 6,332,889 B1 | 12/2001 | Sancoff et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,369,834 B1 | 4/2002 | Zilles et al. |
| 6,371,907 B1 | 4/2002 | Hasegawa et al. |
| 6,371,952 B1 | 4/2002 | Madhani et al. |
| 6,375,471 B1 | 4/2002 | Wendlandt et al. |
| 6,377,011 B1 | 4/2002 | Ben-Ur |
| 6,385,509 B2 | 5/2002 | Das et al. |
| 6,394,998 B1 | 5/2002 | Wallace et al. |
| 6,397,323 B1 | 5/2002 | Yoshida |
| 6,398,726 B1 | 6/2002 | Ramans et al. |
| 6,398,755 B1 | 6/2002 | Belef et al. |
| 6,400,979 B1 | 6/2002 | Stoianovici et al. |
| 6,400,980 B1 | 6/2002 | Lemelson |
| 6,401,572 B1 | 6/2002 | Provost |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,265 B1 | 10/2002 | Evans et al. |
| 6,471,697 B1 | 10/2002 | Lesh |
| 6,485,489 B2 | 11/2002 | Teirstein et al. |
| 6,487,940 B2 | 12/2002 | Hart et al. |
| 6,490,490 B1 | 12/2002 | Uchikubo et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,496,099 B2 | 12/2002 | Wang et al. |
| 6,517,565 B1 | 2/2003 | Whitman et al. |
| 6,522,906 B1 | 2/2003 | Salisbury, Jr. et al. |
| 6,554,844 B2 | 4/2003 | Lee et al. |
| 6,557,558 B1 | 5/2003 | Tajima et al. |
| 6,565,554 B1 | 5/2003 | Niemeyer |
| 6,569,084 B1 | 5/2003 | Mizuno et al. |
| 6,574,355 B2 | 6/2003 | Green |
| 6,587,750 B2 | 7/2003 | Gerbi et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,626,899 B2 | 9/2003 | Houser et al. |
| 6,645,196 B1 | 11/2003 | Nixon et al. |
| 6,659,939 B2 | 12/2003 | Moll et al. |
| 6,669,687 B1 | 12/2003 | Saadat |
| 6,676,684 B1 | 1/2004 | Morley et al. |
| 6,685,698 B2 | 2/2004 | Morley et al. |
| 6,692,485 B1 | 2/2004 | Brock et al. |

(56) References Cited

U.S. PATENT DOCUMENTS

| | | |
|---|---|---|
| 6,695,818 B2 | 2/2004 | Wollschlager |
| 6,699,235 B2 | 3/2004 | Wallace et al. |
| 6,702,826 B2 | 3/2004 | Liddicoat et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B2 | 4/2004 | Wang et al. |
| 6,770,081 B1 | 8/2004 | Cooper et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,810,281 B2 | 10/2004 | Brock et al. |
| 6,817,972 B2 | 11/2004 | Snow |
| 6,817,974 B2 | 11/2004 | Cooper et al. |
| 6,827,712 B2 | 12/2004 | Tovey et al. |
| 6,837,846 B2 | 1/2005 | Jaffe et al. |
| 6,837,883 B2 | 1/2005 | Moll et al. |
| 6,840,938 B1 | 1/2005 | Morley et al. |
| 6,843,793 B2 | 1/2005 | Brock et al. |
| 6,852,107 B2 | 2/2005 | Wang et al. |
| 6,858,003 B2 | 2/2005 | Evans et al. |
| 6,860,877 B1 | 3/2005 | Sanchez et al. |
| 6,860,878 B2 | 3/2005 | Brock |
| 6,911,916 B1 | 6/2005 | Wang et al. |
| 6,936,001 B1 | 8/2005 | Snow |
| 6,936,056 B2 | 8/2005 | Nash et al. |
| 6,949,106 B2 | 9/2005 | Brock et al. |
| 6,951,535 B2 | 10/2005 | Ghodoussi et al. |
| 6,963,792 B1 | 11/2005 | Green |
| 6,994,708 B2 | 2/2006 | Manzo |
| 6,997,931 B2 | 2/2006 | Sauer et al. |
| 7,021,173 B2 | 4/2006 | Stoianovici et al. |
| 7,025,064 B2 | 4/2006 | Wang et al. |
| 7,044,936 B2 | 5/2006 | Harding |
| 7,074,179 B2 | 7/2006 | Wang et al. |
| 7,087,049 B2 | 8/2006 | Nowlin et al. |
| 7,090,683 B2 | 8/2006 | Brock et al. |
| 7,169,141 B2 | 1/2007 | Brock et al. |
| 7,172,580 B2 | 2/2007 | Hruska et al. |
| 7,214,230 B2 | 5/2007 | Brock et al. |
| 7,276,044 B2 | 10/2007 | Ferry et al. |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock et al. |
| 7,608,083 B2 | 10/2009 | Lee et al. |
| 7,615,042 B2 | 11/2009 | Beyar et al. |
| 7,635,342 B2 | 12/2009 | Ferry et al. |
| 7,713,190 B2 | 5/2010 | Brock et al. |
| 7,727,185 B2 | 6/2010 | Weitzner et al. |
| 7,744,608 B2 | 6/2010 | Lee et al. |
| 7,766,856 B2 | 8/2010 | Ferry et al. |
| 7,766,894 B2 | 8/2010 | Weitzner et al. |
| 7,775,972 B2 | 8/2010 | Brock et al. |
| 7,819,884 B2 | 10/2010 | Lee et al. |
| 7,854,738 B2 | 12/2010 | Lee et al. |
| 7,867,241 B2 | 1/2011 | Brock et al. |
| 7,905,828 B2 | 3/2011 | Brock et al. |
| 7,918,861 B2 | 4/2011 | Brock et al. |
| 7,938,809 B2 | 5/2011 | Lampropoulos et al. |
| 7,955,316 B2 | 6/2011 | Weitzner et al. |
| 7,959,557 B2 | 6/2011 | Weitzner et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,114,097 B2 | 2/2012 | Brock et al. |
| 8,157,308 B2 | 4/2012 | Pedersen |
| 8,182,415 B2 | 5/2012 | Larkin et al. |
| 8,187,229 B2 | 5/2012 | Weitzner et al. |
| 8,277,417 B2 | 10/2012 | Fedinec et al. |
| 8,291,791 B2 | 10/2012 | Light et al. |
| 8,414,505 B1 * | 4/2013 | Weitzner ............ A61M 25/0113 600/585 |
| 8,414,598 B2 | 4/2013 | Brock et al. |
| 8,425,465 B2 | 4/2013 | Nagano |
| 8,603,068 B2 | 12/2013 | Weitzner et al. |
| 8,671,817 B1 | 3/2014 | Bogusky |
| 8,671,950 B2 | 3/2014 | Weitzner et al. |
| 8,684,952 B2 | 4/2014 | Weitzner et al. |
| 8,720,448 B2 | 5/2014 | Reis et al. |
| 8,746,252 B2 | 6/2014 | McGrogan et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,204,933 B2 | 12/2015 | Reis et al. |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |
| 2001/0031983 A1 | 10/2001 | Brock |
| 2001/0042643 A1 | 11/2001 | Krueger et al. |
| 2002/0045905 A1 | 4/2002 | Gerbi et al. |
| 2002/0087151 A1 | 7/2002 | Mody et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0120252 A1 | 8/2002 | Brock |
| 2002/0128661 A1 | 9/2002 | Brock |
| 2002/0128662 A1 | 9/2002 | Brock |
| 2002/0138082 A1 | 9/2002 | Brock |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0045888 A1 | 3/2003 | Brock |
| 2003/0056561 A1 | 3/2003 | Butscher et al. |
| 2004/0015053 A1 | 1/2004 | Bieger |
| 2004/0152972 A1 | 8/2004 | Hunter |
| 2004/0243147 A1 | 12/2004 | Lipow |
| 2004/0254566 A1 | 12/2004 | Plicchi |

(56) References Cited

U.S. PATENT DOCUMENTS

| | | |
|---|---|---|
| 2005/0004579 A1 | 1/2005 | Schneider et al. |
| 2005/0183532 A1 | 8/2005 | Najaf et al. |
| 2005/0203382 A1 | 9/2005 | Govari et al. |
| 2005/0222554 A1 | 10/2005 | Wallace et al. |
| 2006/0041245 A1 | 2/2006 | Ferry |
| 2006/0111692 A1 | 5/2006 | Hlavka et al. |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0191177 A1 | 8/2007 | Nagai et al. |
| 2007/0232855 A1 | 10/2007 | Weitzner et al. |
| 2007/0239028 A1 | 10/2007 | Houser |
| 2007/0239178 A1 | 10/2007 | Weitzner et al. |
| 2007/0245175 A1 | 10/2007 | Zheng et al. |
| 2007/0250072 A1 | 10/2007 | Weitzner et al. |
| 2007/0250097 A1 | 10/2007 | Weitzner et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177281 A1 | 7/2008 | Weitzner et al. |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0300592 A1 | 12/2008 | Weitzner et al. |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0105639 A1 | 4/2009 | Weitzner et al. |
| 2009/0105645 A1 | 4/2009 | Kidd et al. |
| 2009/0171371 A1 | 7/2009 | Nixon |
| 2009/0247944 A1 | 10/2009 | Kirschenman et al. |
| 2009/0248039 A1 | 10/2009 | Cooper et al. |
| 2009/0254083 A1 | 10/2009 | Wallace et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0274078 A1 | 10/2010 | Kim et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0144656 A1 | 6/2011 | Lee et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0226227 A1 | 9/2012 | Weitzner et al. |
| 2012/0232476 A1 | 9/2012 | Bhat et al. |
| 2012/0239012 A1 | 9/2012 | Laurent et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0171943 A1 | 6/2014 | Weitzner et al. |
| 2014/0222019 A1 | 8/2014 | Brudnick |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0090063 A1 | 4/2015 | Lantermann et al. |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0151606 A9 | 6/2016 | Weitzner et al. |
| 2016/0157945 A1 | 6/2016 | Madhani |
| 2016/0166234 A1 | 6/2016 | Zhang |
| 2016/0235495 A1 | 8/2016 | Wallace et al. |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |

(56) References Cited

U.S. PATENT DOCUMENTS

| | | |
|---|---|---|
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0104820 A1 | 4/2018 | Troy et al. |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |

FOREIGN PATENT DOCUMENTS

| | | |
|---|---|---|
| DE | 19649082 | 1/1998 |
| DE | 102004020465 | 9/2005 |
| EP | 0683016 | 11/1995 |
| EP | 0776738 | 6/1997 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| WO | WO 93/14704 | 8/1993 |
| WO | WO 98/25666 | 6/1998 |
| WO | WO 9945994 A1 | 9/1999 |
| WO | WO 00/60521 | 10/2000 |
| WO | WO 00/67640 | 11/2000 |
| WO | WO 2002/051329 | 7/2002 |
| WO | WO 02/74178 | 9/2002 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/059412 | 4/2017 |
| WO | WO 17/0151993 | 9/2017 |

OTHER PUBLICATIONS

M.W. Thring, "Robots and Telechirs: Manipulators With Memory; Remote Manipulators; Machine Limbs for the Handicapped", First published in 1983 by Ellis Horwood Limited.

Mayo Clinic, Robotic Surgery, https://www.mayoclinic.org/tests-procedures/robotic-surgery/about/pac-20394974?p=1, downloaded from the internet on Jul. 12, 2018, 2 pp.

\* cited by examiner

CATHETER DRIVER SYSTEM

RELATED APPLICATIONS

This application is a continuation of U.S. patent application Ser. No. 14/189,107, filed Feb. 25, 2014, published as U.S. Patent Application Publication No. 2014/0171943, which is a continuation of U.S. patent application Ser. No. 12/111,119, filed Apr. 28, 2008, now U.S. Pat. No. 8,684,952, which is a continuation of U.S. application Ser. No. 10/270,743, filed Oct. 11, 2002, now U.S. Pat. No. 8,414,505, which claims the benefit of U.S. Provisional Application No. 60/332,287 filed Nov. 21, 2001, and is a continuation-in-part of U.S. application Ser. No. 10/216,067 filed Aug. 8, 2002, now abandoned, which claims the benefit of U.S. Provisional Application No. 60/313,497 filed Aug. 21, 2001, and is a continuation-in-part of U.S. application Ser. No. 10/023,024, now abandoned, Ser. No. 10/011,371, now U.S. Pat. No. 7,090,683, issued Aug. 15, 2006, Ser. No. 10/011,449, now abandoned, Ser. No. 10/010,150, now U.S. Pat. No. 7,214,230, issued May 8, 2007, Ser. No. 10/022,038, now abandoned, Ser. No. 10/012,586, now U.S. Pat. No. 7,371,210, all filed Nov. 16, 2001, and all of which claim the benefit of U.S. Provisional Application Nos. 60/269,200 filed Feb. 15, 2001, 60/276,217 filed Mar. 15, 2001, 60/276,086 filed Mar. 15, 2001, 60/276,152 filed Mar. 15, 2001, and 60/293,346 filed May 24, 2001. The entire teachings of the above applications are incorporated herein by reference.

BACKGROUND

Catheters are used extensively in the medical field in various types of medical procedures, as well as other invasive procedures. In general, minimally invasive medical procedures involve operating through a natural body opening or orifice of a body lumen, or through small incisions, typically 5 mm to 10 mm in length, through which instruments are inserted. In general, minimally invasive surgery is less traumatic than conventional surgery, due, in part, because no incision is required in certain minimally invasive procedures, or the significant reduction in the incision size in other procedures. Furthermore, hospitalization is reduced and recovery periods are shortened as compared with conventional surgical techniques.

Catheters may be provided in a variety of different shapes and sizes depending upon the particular application. It is typical for a clinician to manipulate the proximal end of the catheter to guide the distal end of the catheter inside the body, for example, through a vein or artery. Because of the small size of the incision or opening and the remote location of the distal end of the catheter, much of the procedure is not directly visible to the clinician. Although clinicians can have visual feedback from the procedure site through the use of a video camera or endoscope inserted into the patient, or through radiological imaging or ultrasonic imaging, the ability to control even relatively simple instruments remains difficult.

In some procedures, such as electrophysiology, the surgeon manually places the distal end of an extension, such as a catheter, at a site of interest in the patient's body. The distal end of the catheter can be coupled to an energy generator to treat the site of interest. Alternatively, or additionally, the catheter can be connected to a detector which receives signals from the distal end of the catheter for diagnostic purposes. The catheter is typically connected to a handle that includes control devices such as dials that enable the surgeon to articulate the catheter, and thus, to maneuver the catheter through the patient.

In view of the above, some have proposed using robotic tele-surgery to perform minimally invasive procedures. Typically, these robotic systems use arms that reach over the surgical table and manipulate the surgical instruments inserted into the patient, while the surgeon sits at a master station located a distance from the table and issues commands to the arms.

SUMMARY

An apparatus for performing medical procedures on an anatomical body includes an extension with an element near its distal end to be extended into the body, and a driver that moves the extension axially into the body, and that causes flexure of the distal end of the extension. The movement and flexure of the extension is driven by the driver from the proximal end of the extension, and an electronic controller directs the operation of the driver.

In some embodiments, the driver includes control devices which may include conventional handle dials. A first control device is coupled to a first control wire, and a second control device is coupled to a second control wire. The first and second control wires extend along the length of the extension, and the terminal ends of the first and second control wires are coupled to the distal end of the extension. The first and second control devices are operated to control the flexure movements of the distal end of the extension with at least two degrees-of-freedom. The first and second control devices can be part of a handle which is a plug-in module that is removable from the driver.

In certain embodiments, the driver moves the extension with a rotational movement. The driver may include a first drive mechanism and a second drive mechanism that are coupled to a motor array. The motor array in turn may be coupled to the controller, which directs the operation of the motor array and consequent operation of the drive mechanisms to move the extension with the axial and rotational movements.

In some embodiments, the element may receive RF energy from an RF generator for delivery to a target site in the body. In particular embodiments, the element provides signals from the target site to a detector. The signals are typically related to properties of the target site.

Since the movements of the driver are under the direction of the controller, these movements may be gentler than those produced by the surgeon when the instrument is manually driven through the patient. Furthermore, with the assistance of the driver, the surgeon is less likely to become fatigued during the procedure.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention provides a drive system that can be used to manipulate a surgical implement from its proximal end. For example, a manually operable instrument can be coupled to the drive system without requiring any modification to the instrument. The drive system can be operated by a surgeon at a master station of a master-slave telerobotic system. In some embodiments, the drive apparatus is in the form of a housing in which the instrument is inserted, which is then driven as the surgeon manipulates the housing.

Figure 1:
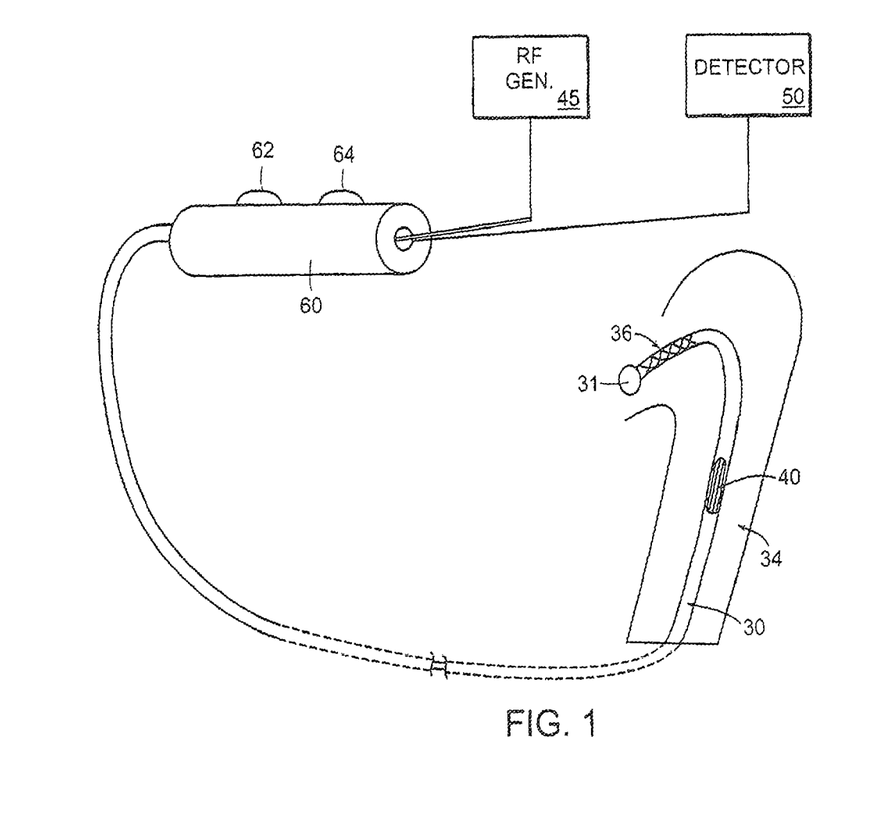
FIG. 1 illustrates a manual catheter system.
Figure 1A:
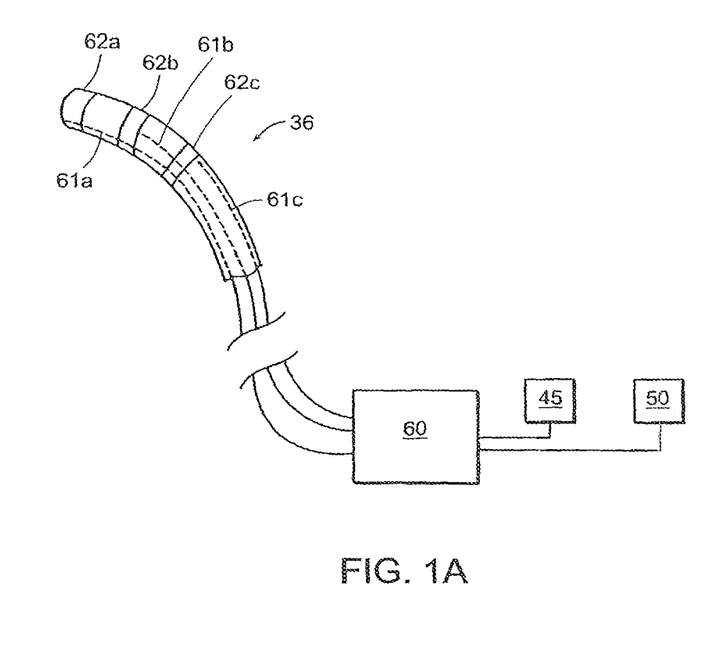
FIG. 1A a close-up view of the terminal end of the catheter shown in FIG. 2.

In electrophysiology procedures, as shown in FIG. 1, a extension such as a catheter 30 is used for diagnostic purposes or sensing conditions at a predetermined target site 31 as the catheter 30 extends through an artery or vein 34. The distal end 36 of the catheter 30 can be considered as an operative segment of the catheter and thus is capable of flexing or bending to assist guiding the catheter through the anatomic body, and curving to a desired location, for example, to lean against an inner surface of the heart. In this regard, there is schematically illustrated wiring 40 that may extend along the length of the catheter 30 that transmits mechanical inputs of a manual handle 60. As shown in FIG. 1A, there can be additional wiring 61a, 61b, and 61c that are connected to respective electrophysiology elements 62a, 62b, and 62c and extend from the distal end 36 to an RF generator 45, as well as a detector 50, associated with the handle 60 (FIG. 1).

In some embodiments, the RF generator 45 couples energy through the handle 60 by way of the catheter 30 to the elements 62a, 62b, and 62c at the distal end 36 for the application of RF energy at the target site 31 for therapeutic purposes. In association with the RF generator 45, the detector 50 may receives signals from a probe, such as the elements 62a, 62b, and 62c, positioned at the target site. Typically, these signals are related to physiological properties at the target site.

As can be seen in FIG. 1, the handle 60 has wheels or dials 62 and 64 that can be manually operated by the surgeon during a procedure. Manipulation of the dials 62 and 64 are transmitted through the control wiring 40 to the distal end 36 to control the flexing or bending of the distal end in respective orthogonal directions.

Figure 2:
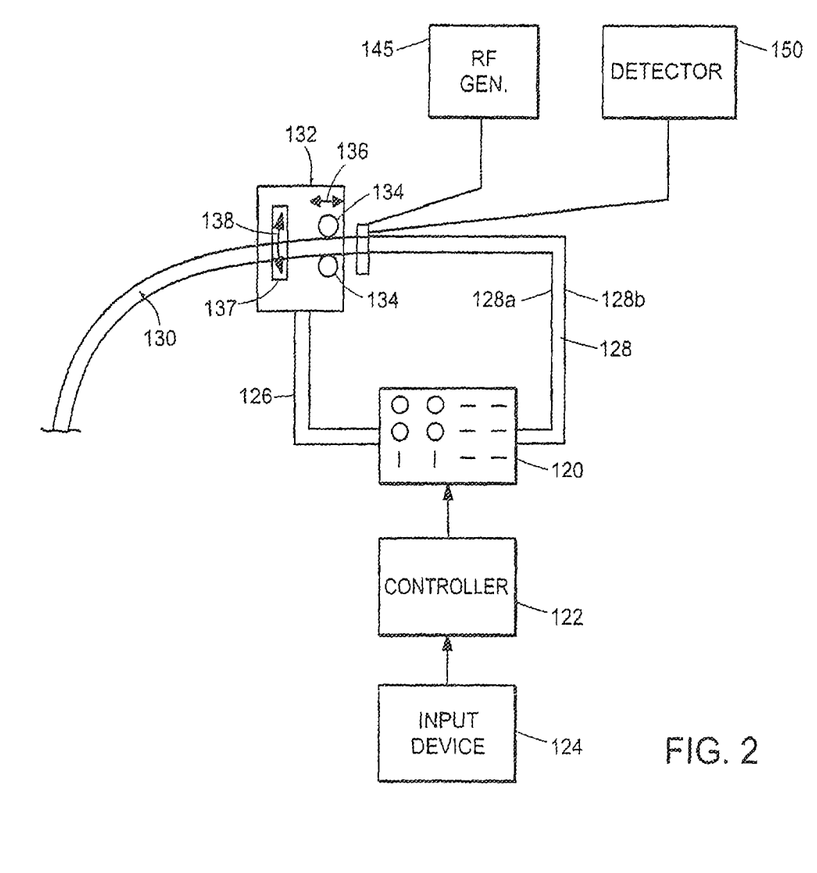
FIG. 2 is a block and schematic diagram of a catheter drive system in accordance with the present invention.

In a particular embodiment, as shown in FIG. 2, the operation of the drive system of FIG. 1 is automated. That is, the system shown in FIG. 2 modifies the construction of that shown in FIG. 1 by providing for automatic control of a catheter 130, which at its distal end is substantially the same as the catheter 30 shown in FIGS. 1 and 1A.

Like the catheter 30, the catheter 130 is able to move at its end with at least two degrees-of-freedom under control of wires 128a and 128b. In addition, the catheter 130 is coupled at its distal end to a support block 132 that includes wheels 134 that provide linear translation of the catheter 130 in the direction 136. A further mechanism 137 provides rotational motion of the catheter 130, such as depicted by the arrow 138. Moreover, there are also wires extending through the catheter 130 associated with the RF generator 145 and the detector 150.

In the embodiment illustrated in FIG. 2, a guide wire is not used, nor is a guide wire used in the device shown in FIGS. 1 and 1A. Accordingly, only a single support block 132 is used with this catheter construction. However, the particular catheter 130 is provided with the flex control, and hence is provided with control wires that extend through the catheter 130 like those described previously in reference with FIG. 1.

As shown in FIG. 2, the support or drive block 132 is coupled to an electromechanical drive member or motor array 120. Also included in the system is an input device 124 at which a surgeon provides control actuations. The input device 124 is coupled to a controller 122 which in turn is coupled to the motor array 120. Thus, instructions from the input device 124 are received by the controller 122 which then directs the operation of the motor array 120.

As mentioned previously, movement of the motors of the array 120 is transmitted to the catheter 130 through mechanically cabling extending through the catheter. In particular, a mechanical cabling 126 coupled directly to the block 132 controls the rotational and linear degrees-of-freedom of the catheter 130 through the mechanism 137 and wheels 134, respectively. In addition, there is a cabling 128 from the motor array 120 to the block 132 which controls the bending and flexing movement of the catheter 130. As such, one cable 128a may be used to control the bending movements of the catheter with one degree-of-freedom, and another cable 128b may control the bending movements with a second degree-of-freedom.

The input device 124 may include separate manipulators for the different movements of the catheter 130. As described in connection with FIG. 1, the input device can take on one of many different forms including joysticks, wheels, dials, and other types of manual interfaces. For the control desired in FIG. 2, one input member controls the mechanical cabling 126 for providing the two degrees-of-freedom of action of the catheter 130, in particular, the linear and rotational movement. Another input member in input device 124 controls the flexing and bending of the catheter 130 by way of the mechanical cabling 128. The input instructions from the input device 124 are transmitted to the motor array 120 by way of the controller 122 which may be a microprocessor.

Figure 2A:
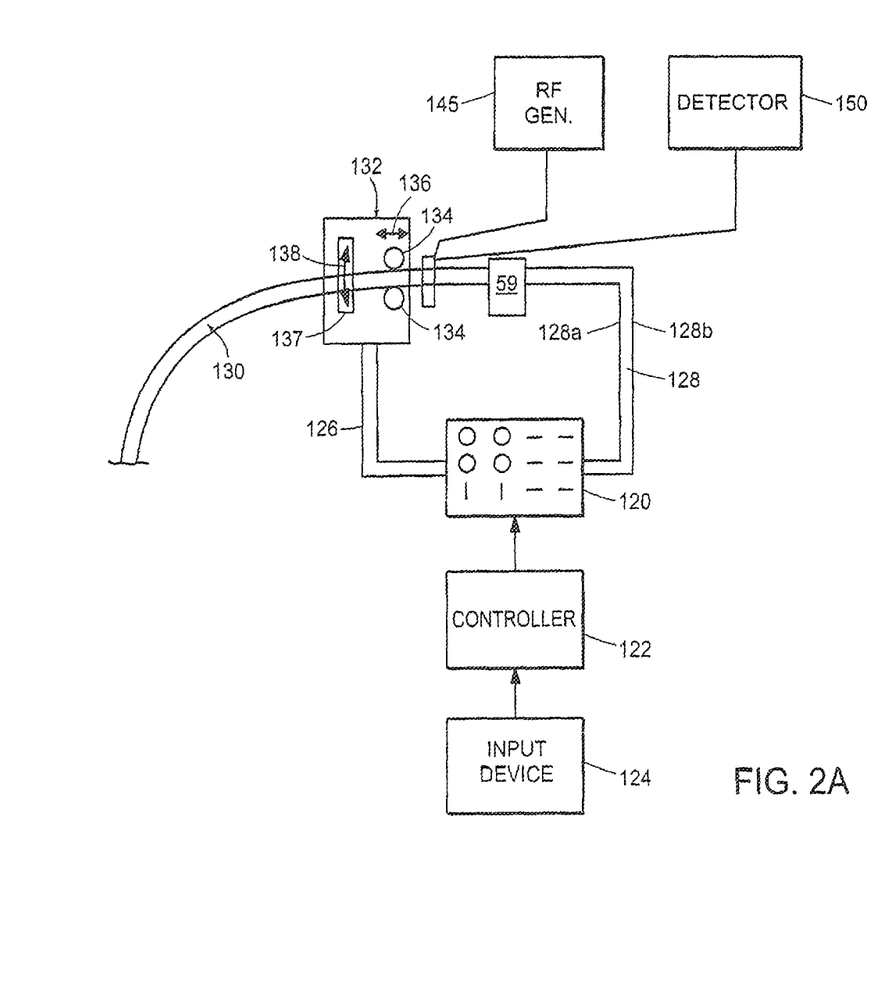
FIG. 2A is a variation of the configuration shown in FIG. 3.

In an alternative arrangement, as shown in FIG. 2A, an intermediate drive device 59 may be interposed between the motor array 120 and the catheter 130. In such an arrangement, the motor array 120 communicates with the drive device 59 over the lines 128, which may be electrical. In turn, the drive device 59 is coupled to the cabling extending through the length of the catheter, and actuates the cabling to cause the distal end of the catheter 130 to bend and flex with one or more degrees-of-freedom.

Details of an automated catheter drive system are describe in the U.S. Application entitled "Coaxial Catheter System," by Weitzer, Rogers, and Solbjor, Ser. No. 10/270,740, filed herewith, the entire contents of which are incorporated herein by reference. Details of a imaging system that aids the movement of the catheter through an anatomic body are describe in the U.S. application entitled "Catheter Tracking System," by Weitzner and Lee, Ser. No. 10/216,669, filed herewith, the entire contents of which are incorporated herein by reference.

Figure 3:
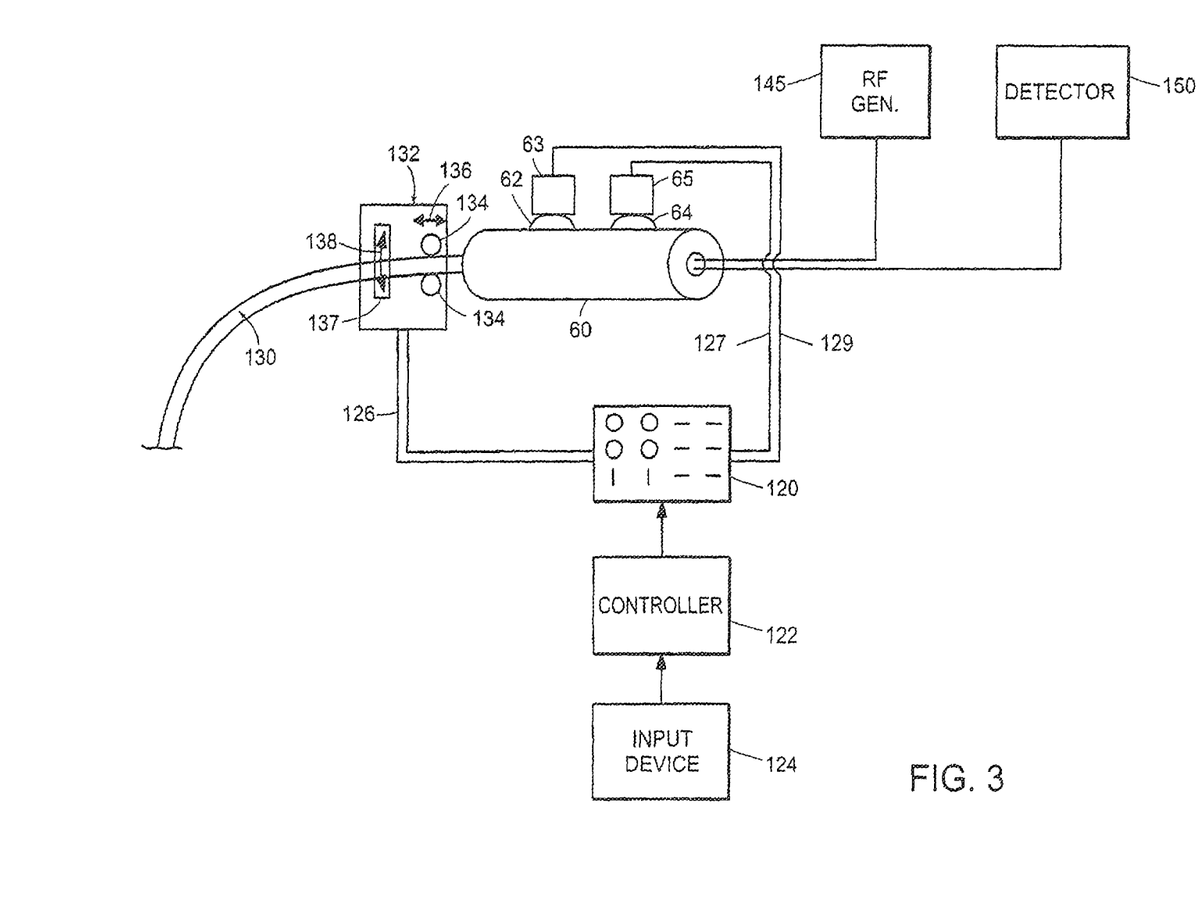
FIG. 3 is a block and schematic diagram of another version of a catheter drive system in accordance with the present invention.

Referring now to FIG. 3, there is shown a further embodiment of a catheter drive system. In FIG. 3, like reference characters are used to identify like features shown in FIG. 2. Thus, in the embodiment of FIG. 3, there is an input device 124, a controller 122, and a motor array 120. FIG. 3 also depicts the support block 132 which provides both linear and rotational movement of the catheter 130. As before, these movements are provide by wheels 134 for the linear translation as noted by the arrow 136, and the member or mechanism 137 for the rotational translation as noted by the arrow 138.

In the embodiment of FIG. 3, the handle 60 is depicted with its pair of actuating wheels or dials 62 and 64 shown earlier in FIG. 1. Rather than replacing the handle 60, as in the embodiment of FIG. 2, the handle 60 here remains intact so that the wheels 62 and 64 are used to control the flexing and bending of the catheter 130. For this purpose, there are included drive pieces 63 and 65 associated, respectively, with the wheels 62 and 64. Each of the drive pieces engages its corresponding wheel to drive the wheels in either direction to provide the appropriate flex control of the catheter 130. Note in FIG. 3, the separate lines 127 and 129, which may be mechanical or electrical, coupling the drive pieces 65 and 63 to the motor array 120. Hence, actuation of respective drive units in the motor array 120 results in a consequent actuation of the wheels 62 and 64 via the control line 129 and drive piece 63, and the control line 127 and drive piece 65, respectively. Note that with this embodiment the proper support and housings are provided such that the drive pieces 63 and 65 maintain proper engagement with the wheels 62 and 64.

With the particular arrangement shown in FIG. 3, the existing catheter construction need not be modified. Rather, the drive system shown in FIG. 3 is simply coupled to an existing catheter system, such as the handle 60 and catheter 130 combination.

Although the motor array 120 is illustrated as having two separate lines for two separate drive pieces, in other embodiments, the handle 60 may have only a single control dial. In such implementations, there may be only a single line and associated drive piece that couples the motor array 120 to the handle 60. Thus, unlike the handle 60 with wheels 62 and 64 which provide flex control in orthogonal planes, if only a single wheel is used, the catheter typically flexes only in a single plane. However, in arrangements in which the catheter support block 132 provides for rotational movement of the catheter 130, the movement of the catheter is not limited to this single plane, since as the catheter is being rotated it moves out of this plane.

Figure 4:
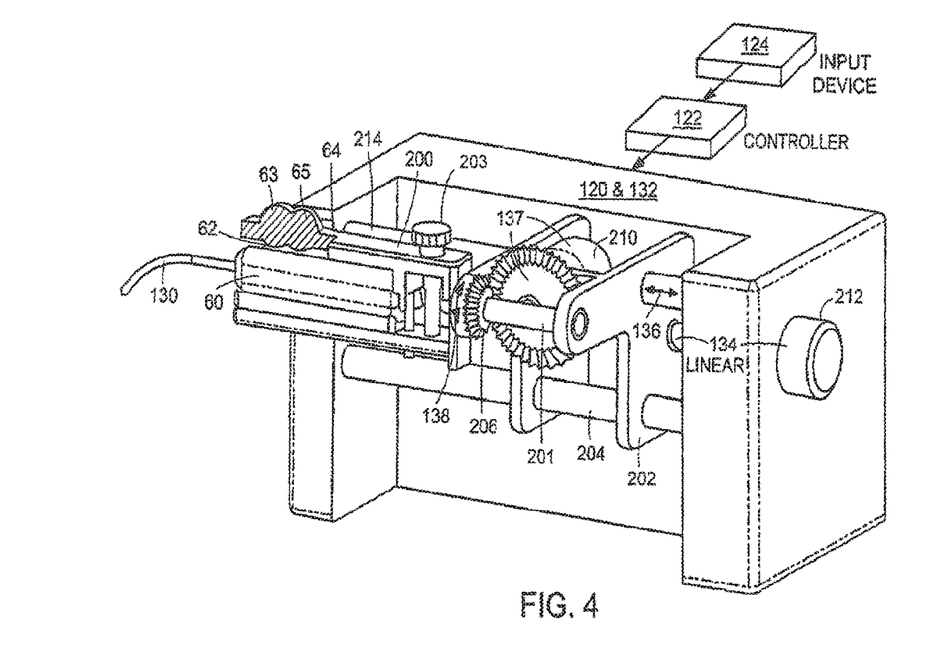
FIG. 4 is a perspective view of an illustrative embodiment of the catheter drive system of FIG. 3.
Figure 4A:
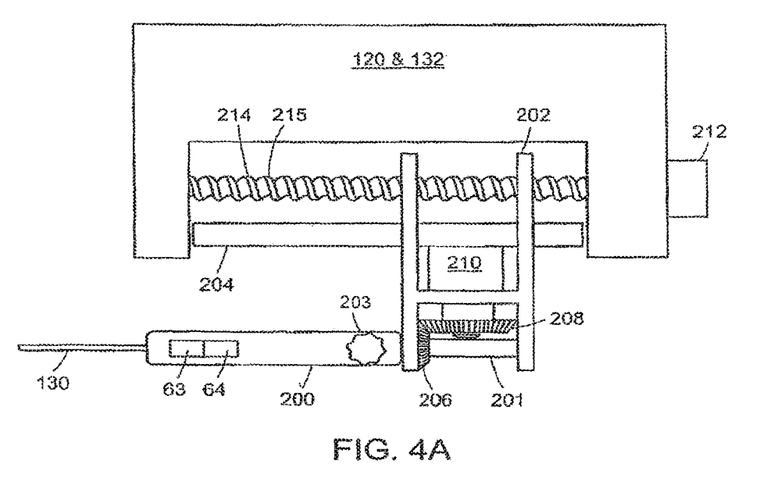
FIG. 4A is a top view of the catheter drive system of FIG. 4.
Figure 4B:
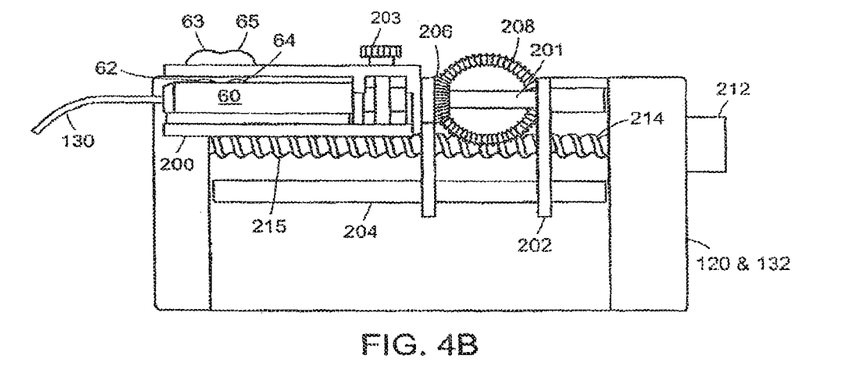
FIG. 4B is a front view of the catheter drive system of FIG. 4.

A particular embodiment of the system of FIG. 3 is illustrated in FIGS. 4, 4A, and 4B, where like reference characters are used to identify like features shown in FIG. 3. In this embodiment, the handle 60 is clamped in a clamp or vise 200 with a screw 202. The clamp 200 is connected to a shaft 201 supported in a carriage 202 that moves back and forth on a guide bar 204 mounted in the drive block 132. Associated with the shaft 201 is a set of gears 206 that engage with another set of gears 208 of the rotary drive mechanism 137. The drive mechanism 137 includes a motor 210 driven by the array 120 located in the drive block 132 and under the direction of the controller 122 as it receives instructions from the user through the input device 124. Thus, as the motor 210 rotates the gears 208, a consequent rotary motion is induced in the gears 206 to rotate the clamp 200, and hence the handle 60 and catheter 130, in the rotational direction 138.

The linear drive mechanism 134 of this embodiment includes a motor 212 connected to a screw drive 214. The motor 212 and screw drive 214 are mounted to the drive block 132 in a manner to allow the screw drive 214 to rotate. The screw drive 214 has threads 215 about its periphery that engage with the carriage 202. Accordingly, under the direction of the controller 122 via the array 120, the motor 212 rotates the screw drive 214 to induce the carriage 202, and hence the handle 60 and catheter 130, to move back and forth in the linear direction 136.

As previously mentioned, the drive pieces 63 and 65 engage with the dials or wheels 62 and 64 of the handle 60 so that upon instructions from the user through the input device 124, the drive pieces 63 and 65 manipulate the dials 62 and 64 to control the desired bending and flexing movements of the catheter 130.

This invention can be implemented and combined with other applications, systems, and apparatuses, for example, those discussed in greater detail in U.S. Provisional Application No. 60/332,287, filed Nov. 21, 2001, the entire contents of which are incorporated herein by reference, as well as those discussed in greater detail in each of the following documents, all of which are incorporated herein by reference in their entirety:

U.S. application Ser. No. 09/783,637 filed Feb. 14, 2001, which is a continuation of PCT application Serial No. PCT/US00/12553 filed May 9, 2000, which claims the benefit of U.S. Provisional Application No. 60/133,407 filed May 10, 1999; U.S. application entitled "Articulated Apparatus for Telemanipulator System," by Brock and Lee, Ser. No. 10/208,087, filed Jul. 29, 2002, which is a continuation of U.S. application Ser. No. 09/827,503 filed Apr. 6, 2001, which is a continuation of U.S. application Ser. No. 09/746,853 filed Dec. 21, 2000, which is a divisional of U.S. application Ser. No. 09/375,666 filed Aug. 17, 1999, now U.S. Pat. No. 6,197,017 which issued on Mar. 6, 2001, which is a continuation of U.S. application Ser. No. 09/028,550 filed Feb. 24, 1998, which is now abandoned; PCT application Serial No. PCT/US01/11376 filed Apr. 6, 2001, which claims priority to U.S. application Ser. No. 09/746,853 filed Dec. 21, 2000, and U.S. application Ser. No. 09/827,503 filed Apr. 6, 2001; U.S. application Ser. Nos. 10/014,143, 10/012,845, 10/008,964, 10/013,046, 10/011,450, 10/008,457, and 10/008,871, all filed Nov. 16, 2001 and all of which claim benefit to U.S. Provisional Application No. 60/279,087 filed Mar. 27, 2001; U.S. application Ser. No. 10/077,233 filed Feb. 15, 2002, which claims the benefit of U.S. Provisional Application No. 60/269,203 filed Feb. 15, 2001; U.S. application Ser. No. 10/097,923 filed Mar. 15, 2002, which claims the benefit of U.S. Provisional Application No. 60/276,151 filed Mar. 15, 2001; U.S. application Ser. No. 10/034,871 filed Dec. 21, 2001, which claims the benefit of U.S. Provisional Application No. 60/257,816 filed Dec. 21, 2000; U.S. application Ser. No. 09/827,643 filed Apr. 6, 2001, which claims the benefit of U.S. Provisional Application No. 60/257,869 filed Dec. 21, 2000, and U.S. Provisional Application No. 60/195,264 filed Apr. 7, 2000.

While this invention has been particularly shown and described with references to preferred embodiments thereof, it will be understood by those skilled in the art that various changes in form and details may be made therein without departing from the scope of the invention encompassed by the appended claims. For example, the catheter need not be limited for use in electrophysiology procedures. That is, there may be other types of probes or end effectors located at the distal end of the catheter. The end effector may be, for example, an articulated tool such as a grasper, scissor, needle holder, micro dissector, staple applier, tacker, suction irrigation tool, and clip applier. The end effector can also be a non-articulated tool, such as a cutting blade, probe, irrigator, catheter or suction orifice, and dilation balloon.

What is claimed is:

1. A medical instrument system comprising:
   an instrument comprising an elongate body having a proximal end and a distal end, a first control wire and a second control wire, the first and second control wires coupled to a distal end of the elongate body and extending through the elongate body, the first and second control wires configured to control movement of the distal end of the elongate body in at least two degrees of freedom;
   a handle part comprising a first control device coupled to the first control wire and a second control device coupled to the second control wire, the first and second control devices comprising first and second non-coaxial, rotatable bodies;
   a manipulator configured to generate an input signal corresponding to a desired movement of the distal end of the instrument in response to a user actuation of the manipulator;
   a controller coupled to the manipulator, the controller configured to generate a control signal in response to the input signal received from the manipulator; and
   a driver comprising a housing configured to receive the handle part releasably coupled to the driver, the driver including a first driver mechanism that engages the first rotatable body, a second driver mechanism that engages the second rotatable body, the housing configured to align the first driver mechanism with the first rotatable body and to align the second driver mechanism with the second rotatable body, and a motor array that is coupled to the first and second driver mechanisms, the motor array coupled to the controller such that the control signal from the controller can direct operation of the motor array and corresponding operations of the first and second driver mechanisms to actuate the first and second control wires and control movement of the distal end of the instrument in the at least two degrees of freedom, wherein the driver includes a first actuator to provide linear motion of the instrument and a second actuator to provide rotational motion of the instrument.

2. The medical instrument system of claim 1, wherein the manipulator comprises at least one of a joystick, wheel, and dial.

3. The medical instrument system of claim 1, wherein the distal end of the elongate body comprises one or more sensors.

4. The medical instrument system of claim 3, wherein the one or more sensors are configured to apply radiofrequency energy at a target site within a patient to diagnose physiological properties at the target site.

5. The medical instrument system of claim 1, wherein the distal end of the elongate body comprises one or more energy transmitters.

6. The medical instrument system of claim 5, wherein the one or more energy transmitters are configured to apply radiofrequency energy at a target site within a patient for therapeutic purposes.

7. The medical instrument system of claim 1, wherein the at least two degrees of freedom comprise a first degree of freedom and a second degree of freedom, wherein the first degree of freedom is orthogonal to the second degree of freedom.

8. The medical instrument system of claim 1, wherein the first and second control devices are configured to be manually actuated.

9. The medical instrument system of claim 8, wherein the first and second control devices each comprise at least one of a wheel and a dial.

10. The medical instrument system of claim 1, wherein the driver is configured to operate the first driver mechanism and the second driver mechanism independent of each other.

11. The medical instrument system of claim 1, wherein the first and second control wires are configured to control the movements of the distal end of the elongate body independent of each other.

12. A method for driving a medical instrument comprising:
    releasably receiving into a housing of a driver, a handle part of the medical instrument that includes first and second non-coaxial rotatable bodies, the first rotatable body coupled to a first control wire of the medical instrument and the second rotatable body coupled to a second control wire of the medical instrument;
    receiving, from an user input device, an input signal corresponding to a desired movement of a distal end of the medical instrument;
    generating a control signal in response to the input signal; and
    in response to the control signal, actuating a first driver mechanism and a second driver mechanism that are coupled to a motor array of the driver to rotate the first rotatable body with the first driver mechanism and to rotate the second rotatable body with the second driver mechanism to actuate the first and second control wires of the medical instrument to control movement of the distal end of the medical instrument corresponding to the desired movement in at least two degrees of freedom, wherein the driver includes a first actuator to provide linear motion of the instrument and a second actuator to provide rotational motion of the instrument, wherein the housing is configured to align the first driver mechanism with the first non-coaxial rotatable body and to align the second driver mechanism with the second non-coaxial rotatable body.

13. The method of claim 12, wherein the user input device comprises at least one of a joystick, wheel, and dial.

14. The method of claim 12, wherein the distal end of the medical instrument comprises one or more sensors.

15. The method of claim 12, wherein the first and second rotatable bodies are configured to be manually actuated.

16. The method of claim 12, wherein the at least two degrees of freedom comprise a first degree of freedom and a second degree of freedom, wherein the first degree of freedom is orthogonal to the second degree of freedom.

17. The method of claim 12, comprising actuating the first driver mechanism and the second driver mechanism independent of each other.

18. The method of claim 12, wherein the first and second control wires are configured to control the movement of the distal end of the medical instrument independent of each other.

* * * * *